United States Patent [19]

Sakamoto et al.

[11] Patent Number: 5,275,949
[45] Date of Patent: Jan. 4, 1994

[54] PROCESS FOR THE PREPARATION OF D-PANTOLACTONE

[75] Inventors: Keiji Sakamoto, Kanazawa; Hideaki Yamada; Sakayu Shimizu, both of Kyoto, all of Japan

[73] Assignee: Fuji Yakuhin Kogyo Kabushiki Kaisha, Toyama, Japan

[21] Appl. No.: 671,799

[22] PCT Filed: Jul. 27, 1990

[86] PCT No.: PCT/JP90/00960
§ 371 Date: Apr. 1, 1991
§ 102(e) Date: Apr. 1, 1991

[87] PCT Pub. No.: WO91/02081
PCT Pub. Date: Feb. 21, 1991

[30] Foreign Application Priority Data

Aug. 3, 1989 [JP] Japan .................. 1-200347

[51] Int. Cl.$^5$ .......................... C12P 41/00; C12P 7/40
[52] U.S. Cl. .................................. 435/280; 435/126; 435/171; 435/136; 435/254.1; 435/256.1; 435/256.5; 435/256.3; 435/256.6
[58] Field of Search ............... 435/123, 171, 126, 136, 280, 254

[56] References Cited

U.S. PATENT DOCUMENTS

| | | | |
|---|---|---|---|
| 3,600,279 | 8/1971 | Takahashi et al. | 435/280 |
| 3,850,750 | 11/1974 | Lanziolotta | 435/126 |

FOREIGN PATENT DOCUMENTS

| | | | |
|---|---|---|---|
| 0006396 | 2/1971 | Japan | 435/126 |
| 0019745 | 6/1972 | Japan | 435/126 |
| 0152895 | 9/1982 | Japan | 435/126 |
| 0098695 | 6/1984 | Japan | 435/126 |
| 0199388 | 10/1985 | Japan | 435/126 |
| 0199391 | 10/1985 | Japan | 435/123 |
| 61-293386 | of 1986 | Japan | . |
| 1242586 | 10/1986 | Japan | 435/126 |
| 2294092 | 12/1987 | Japan | 435/126 |
| 1010996 | 1/1989 | Japan | 435/126 |
| 1198530 | 7/1970 | United Kingdom | 435/280 |

Primary Examiner—Marian C. Knode
Attorney, Agent, or Firm—Birch, Stewart, Kolasch & Birch

[57] ABSTRACT

A process for the preparation of D-pantolactone, comprising employing specific microorganisms to convert D,L-pantolactone as the starting material into D-pantoic acid by selective asymmetric hydrolysis of the D-form only in the D,L-pantolactone, and then separating D-pantoic acid and converting it into D-pantolactone.

17 Claims, No Drawings

PROCESS FOR THE PREPARATION OF D-PANTOLACTONE

FIELD OF INDUSTRIAL APPLICATION

The present invention relates to a process for the preparation of D-pantolactone, a useful intermediate in the preparation of D-pantothenic acid and pantethine, both useful as vitamins of medical or physiological importance.

PRIOR ART

D-pantolactone has heretofore been prepared through optical resolution of chemically synthesized D,L-pantolactone.

Such process, however, requires the use of costly resolving agents such as quinine or brucine, and has the disadvantage that the recovery of D-pantolactone is not easily carried out.

Processes of enzymatically resolving D,L-pantolactone are also known, and the following processes have heretofore been reported:

In Japanese Examined Patent Application Publication No. 19745/72 (TOKKO-SHO 47-19745) is described a process of obtaining only D-pantolactone by using microorganisms to completely decompose L-pantolactone in D,L-pantolactone. This process, however, has the drawback that half the amount of D,L-lactone is lost.

In Japanese Unexamined Patent Application Publication No. 293386/86 (TOKKAI-SHO 61-293386) is described a process wherein only L-pantolactone in D,L-pantolactone is oxidized by the use of microorganisms into ketopantolactone, which is then converted by asymmetric reduction into D-pantolactone. This process, however, is of little practical significance due to the fact that both the substrate concentration and the reaction rate are low.

In Japanese Unexamined Patent Application Publication Nos. 152895/82 (TOKKAI-SHO 57-152895) and 294092/87 (TOKKAI-SHO 62-294092) are described processes wherein the L-form in D,L-pantolactone is selectively subjected to asymmetric hydrolysis by microorganisms to afford D-pantolactone. These processes are not practical because both the substrate concentration and the reaction rate are low, and D-pantolactone of high optical purity can be obtained only when the L-form has been completely hydrolyzed.

DISCLOSURE OF THE INVENTION

As a result of extensive researches on the asymmetric hydrolysis of D,L-pantolactone, the present inventors have now found that D-pantolactone can be obtained efficiently from D,L-pantolactone through selective asymmetric hydrolysis by certain microorganisms of only the D-form in D,L-pantolactone to form D-pantoic acid, followed by separation and conversion thereof into D-pantolactone. The present invention has been predicated on such findings.

Accordingly, the present invention provides a process for the preparation of D-pantolactone, comprising selectively subjecting the D-form in D,L-pantolactone to asymmetric hydrolysis employing a microorganism possessing the ability to effect said selective asymmetric hydrolysis selected from the group consisting of the genera Fusarium, Cylindrocarpon, Gibberella, Aspergillus, Penicillium, Rhizopus, Volutella, Gliocladium, Eurotium, Nectria, Schizophyllum, Myrothecium, Neurospora, Acremonium, Tuberculina, Absidia, Sporothrix, Verticillium and Arthroderma to form D-pantoic acid, which is then separated and converted into D-pantolactone, followed by recovery thereof.

As compared to the above-mentioned known processes of selective asymmetric hydrolysis of the L-form in D,L-pantolactone, the present invention has many advantages. For example higher substrate concentrations may be used, shorter reaction times may be employed, and D-pantolactone of extremely high optical purity can be obtained.

The following describes the present invention in more detail.

The inventors inoculated 5 ml portions of different liquid media with seed cultures from slants. The seeded media were subjected to aerobic shake culture at 28° C. for 2-7 days and then to centrifugation or filtration to collect the cells. To the cells were added 2 ml of 2% D,L-pantolactone solution in 0.2M Tris-HCl buffer, and the mixture was shaken overnight at 28° C. The resultant reaction liquid was subjected to HPLC and GLC to measure the decrease of pantolactone and the amount of pantoic acid formed, and to determine the optical purity of pantolactone, respectively.

As a result thereof, it has been found that microorganisms with the ability to carry out asymmetric hydrolysis which belong to the genera Fusarium, Cylindrocarpon, Gibberella, Aspergillus, Penicillium, Rhizopus, Volutella, Gliocladium, Eurotium, Nectria, Schizophyllum, Myrothecium, Neurospora, Acremonium, Tuberculina, Absidia, Sporothrix, Verticillium or Arthroderma have suitable properties for the D-form-selective asymmetric hydrolysis and for the industrial production of D-pantolactone.

Among microorganisms belonging to each of the genera mentioned above can be found those that exhibit a particularly outstanding ability to carry out the D-form-selective asymmetric hydrolysis.

In the process according to the present invention, conditions under which to cultivate the microorganisms will vary with the strain used. With regard to media, there are used such media which contain saccharides such as glucose or sucrose, alcohols such as ethanol or glycerol, fatty acids such as oleic acid, or stearic acid or esters thereof, or oils such as rapeseed oil or soybean oil as carbon sources; ammonium sulfate, sodium nitrate, peptone, Casamino acids, corn steep liquor, bran, yeast extract or the like as nitrogen sources; magnesium sulfate, sodium chloride, calcium carbonate, potassium monohydrogen phosphate, potassium dihydrogen phosphate or the like as inorganic salt sources; and malt extract, meat extract or the like as other nutrient sources. The cultivation is carried out aerobically, normally for an incubation period of 1-7 days at a medium pH of 3-9 and an incubation temperature of 10°-50° C.

Microorganisms to be used in the process of the present invention may be in any form, for example, cultures obtained by cultivation of strains in liquid media, cells separated from liquid cultures, dried cells obtained by processing cells or cultures, or immobilized cells.

The operation may be carried out batchwise, semibatchwise or continuously. The concentration of D,L-pantolactone used is normally 10–500 g/l. The reaction temperature is normally 10°–50° C. and the reaction time, in the case of batchwise operation, is normally several hours to three days. The pH of the reaction system is normally of the order of 3-8.

As a result of the D-form-selective asymmetric hydrolysis of D,L-pantolactone by microorganisms, D-pantoic acid is formed with the pH of the reaction liquid being lowered and the reaction rate being decreased concomitantly. In order to maintain higher reaction rates it is desirable for the reaction liquid to be maintained at a pH optimal for the particular microorganism's lactone-hydrolyzing enzyme. For this purpose, hydroxides or carbonates of alkaline or alkaline earth metals, as well as aqueous ammonia or the like, are used as inorganic bases with which to maintain pH.

After the reaction has been completed, L-pantolactone in the reaction liquid which has not undergone hydrolysis is separated, for example through extraction with organic solvents. D-pantoic acid remaining in the reaction liquid is then heated under acidic conditions for conversion into D-pantolactone. The resultant D-pantolactone is recovered by extraction with organic solvents. The recovered L-pantolactone is racemized in any conventional manner for conversion into D,L-pantolactone. This D,L-pantolactone may be used anew by recycling it as the starting material for the process according to the present invention.

The following examples are given to illustrate the present invention more specifically, but the invention is in no way restricted to these examples.

EXAMPLE NOS. 1–19

A liquid medium (pH 6.5) consisting of 1% glucose, 0.5% peptone, 0.5% yeast extract and 0.5% corn steep liquor was dispensed in 5 ml portions into test tubes, and then heat-sterilized by autoclaving at 121° C. for 20 minutes. The various strains mentioned in Table 1 were each inoculated from slants into the medium in the test tubes, and subjected to aerobic shake culture at 28° C. for 5 days. After the cultivation, cells were collected by filtration. Into containers each containing different collected cells was dispensed a 2% D,L-pantolactone solution in Tris-HCl buffer (pH 7.5) in 2 ml portions, and the containers were shaken overnight at 28° C. After the reaction, cells were removed by filtration, and each reaction liquid was subjected to HPLC (Nucleosil 5C$_{18}$ $\phi$ 4.6×1 150 mm; eluent 10% methanol; rate of flow 1 ml/min; wavelength for detection 230 nm) to determine the decrease in pantolactone and the amount of pantoic acid formed. Unreacted pantolactone in the reaction liquid is separated by extraction with ethyl acetate, and pantoic acid remaining in the reaction liquid is then heated under acidification with hydrochloric acid for lactonization. The resultant D-pantolactone was extracted with ethyl acetate. The optical purity of the D-pantolactone thus obtained from the pantoic acid was measured by GLC (*Analytical Biochemistry* 112, 9–19 (1981)). The results are as shown in Table 1.

TABLE 1

| Example No. | Identification of the Strain | Rate of Hydrolysis in % | Optical Purity of D-pantolactone in % e.e. |
|---|---|---|---|
| 1 | Fusarium oxysporum IFO 5942 | 30.1 | 91.2 |
| 2 | Cylindrocarpon tonkinense IFO 30561 | 25.4 | 95.1 |
| 3 | Gibberella fujikuroi IFO 6349 | 27.2 | 93.7 |
| 4 | Aspergillus awamori IFO 4033 | 13.8 | 81.7 |
| 5 | Penicillium chrysogenum IFO 4626 | 30.9 | 79.3 |
| 6 | Rhizopus oryzae IFO 4706 | 15.4 | 77.1 |
| 7 | Volutella buxi IFO 6003 | 9.0 | 77.4 |
| 8 | Gliocladium catenulatum IFO 6121 | 4.0 | 72.1 |
| 9 | Eurotium chevalieri IFO 4334 | 30.0 | 67.2 |
| 10 | Nectria elegans IFO 7187 | 12.3 | 75.0 |
| 11 | Schizophyllum commune IFO 4928 | 18.5 | 76.5 |
| 12 | Myrothecium roridum IFO 9531 | 9.2 | 64.3 |
| 13 | Neurospora crassa IFO 6067 | 14.5 | 42.5 |
| 14 | Acremonium fusidioides IFO 6813 | 23.3 | 49.2 |
| 15 | Tuberculina persicina IFO 6464 | 9.6 | 40.1 |
| 16 | Absidia lichtheimi IFO 4009 | 22.2 | 34.8 |
| 17 | Sporothrix schenckii IFO 5983 | 11.6 | 32.4 |
| 18 | Verticillium malthousei IFO 6624 | 9.1 | 49.6 |
| 19 | Arthroderma uncinatum IFO 7865 | 10.8 | 34.3 |

N.B.: IFO No. stands for No. in the Catalog issued by ZAIDAN-HOJIN HAKKO-KENKYU-SHO (Institute for Fermentation Osaka, a juridical foundation)

EXAMPLE NOS. 20–23

Using 500 ml shake flasks each containing 100 ml of a liquid medium (pH 5.5) consisting of 2% glycerol, 0.5% peptone, 0.5% yeast extract and 0.5% corn steep liquor, the different strains mentioned in Table 2 were each subjected to aerobic shake culture at 28° C. for 6 days. After the cultivation, the different cells were collected by filtration and placed separately in containers. To these containers were added 25 ml portions of a 30% aqueous D,L-pantolactone solution. The reaction liquid was kept at a pH of 6.5–7.5 while adding dropwise 28% aqueous ammonia with stirring, and the reaction was allowed to proceed at 28° C. for 2 days. After-treatment was carried out in the same manner as in Example Nos. 1–19. The yields in terms of amount and percentage and $[\alpha]_D^{20}$ are shown in Table 2 for D-pantolactone obtained and L-pantolactone recovered.

TABLE 2

| Example No. | Identification of the strain | D-Pantolactone formed | | | L-Pantolactone formed | | |
|---|---|---|---|---|---|---|---|
| | | Yielding in g | Yielding in % | $[\alpha]_D^{20}$ (c = 2, Water) | Yielding in g | Yielding in % | $[\alpha]_D^{20}$ (c = 2, Water) |
| 20 | Fusarium oxysporum IFO 5942 | 2.76 | 36.8 | −45.6° | 4.42 | 58.9 | +29.4° |
| 21 | Fusarium semitectum IFO 30200 | 2.66 | 35.5 | −44.1° | 4.19 | 55.9 | +24.6° |
| 22 | Cylindrocarpon tonkinense | 1.70 | 22.7 | −45.1° | 5.16 | 68.8 | +13.6° |

TABLE 2-continued

| Example No. | Identification of the strain | D-Pantolactone formed | | | L-Pantolactone formed | | |
|---|---|---|---|---|---|---|---|
| | | Yielding in g | Yielding in % | $[\alpha]_D^{20}$ (c = 2, Water) | Yielding in g | Yielding in % | $[\alpha]_D^{20}$ (c = 2, Water) |
| | IFO 30561 | | | | | | |
| 23 | Gibberella fujikuroi IFO 6349 | 2.53 | 33.7 | −44.3° | 4.44 | 59.2 | +23.8° |

N.B.: IFO No. stands for No. in the Catalog issued by ZAIDAN-HOJIN HAKKO-KENKYU-SHO (Institute for Fermentation Osaka, a juridical foundation)

We claim:

1. A process for preparing D-pantolactone, comprising subjecting D,L-pantolactone to selective asymmetric hydrolysis by contacting said D,L-pantolactone with a microorganism possessing the ability to effect selective asymmetric hydrolysis of only D-pantolactone in said D,L-pantolactone selected from the group consisting of the genera Fusarium, Cylindrocarpon, Gibberella, Aspergillus, Volutella, and Gliocladium to produce D-pantoic acid, and then separating said D-pantoic acid from the reaction medium, converting it into D-pantolactone, and recovering said D-pantolactone, 2. The process of claim 1, wherein said microorganism is grown aerobically in a medium for a period of 1 to 7 days, at a pH of 3 to 9, at a temperature of 10° to 50° C.

3. The process of claim 2, wherein said carbon source is selected from the group consisting of a saccharide, an alcohol, a fatty acid, a fatty acid ester, and an oil.

4. The process of claim 3, wherein said saccharide is selected from the group consisting of glucose and sucrose, said alcohol is selected from the group consisting of ethanol and glycerol, said fatty acid is selected from the group consisting of oleic acid and stearic acid, said fatty acid ester is selected from the group consisting of an ester of oleic acid and an ester of stearic acid, and said oil is selected from the group consisting of rapeseed oil and soybean oil; said nitrogen source is at least one member selected from the group consisting of ammonium sulfate, sodium nitrate, peptone, Casamino acids, corn steep liquor, bran and yeast extract; and said other nutrient source is at least one member selected from the group consisting of malt extract and meat extract.

5. The process of claim 1, wherein said microorganism is in a form selected from the group consisting of a culture obtained by cultivation of a strain thereof in a liquid medium, cells separated from a liquid culture, dried cells obtained by processing cells or cultures, and immobilized cells.

6. The process of claim 1, wherein said process is carried out batchwise, semi-batchwise, or continuously.

7. The process of claim 1, wherein the concentration of D,L-pantolactone in said reaction medium is initially from 10 to 500 g/l.

8. The process of claim 6, wherein said batchwise process is carried out for a time in the range of from several hours to three days.

9. The process of claim 2, wherein the pH of the reaction system is in the range from 3 to 8.

10. The process of claim 1, wherein the reaction system is maintained at a pH optimal for the activity of the enzyme responsible for catalyzing said selective asymmetric hydrolysis.

11. The process of claim 10, wherein said optimal pH is maintained by employing an inorganic base.

12. The process of claim 11, wherein said inorganic base is selected from the group consisting of a hydroxide of an alkaline metal, a hydroxide of an alkaline earth metal, a carbonate of an alkaline metal, a carbonate of an alkaline earth metal, and aqueous ammonia.

13. The process of claim 1, wherein unreacted L-pantolactone remaining in the reaction medium is removed via extraction with a first organic solvent, the D-pantoic acid remaining in the reaction medium is then heated under acidic conditions to convert it to D-pantolactone, and said D-pantolactone is recovered via extraction with a second organic solvent.

14. The process of claim 13, wherein said L-pantolactone is racemized to produce D,L-pantolactone.

15. The process of claim 13, wherein said first organic solvent is ethyl acetate and said second organic solvent is ethyl acetate.

16. A process for preparing D-pantolactone, comprising subjecting D,L-pantolactone to selective asymmetric hydrolysis by contacting said D,L-pantolactone with a microorganism possessing the ability to effect selective asymmetric hydrolysis of only D-pantolactone in said D,L-pantolactone selected from the group consisting of Absidia lichtheimi IFO 4009,
Acremonium fusidioides IFO 6813,
Arthroderma uncinatum IFO 7865
Aspergillus awamori IFO 4033,
Cylindrocarpon tonkinense IFO 30561,
Eurotium chevalieri IFO 4334,
Fusarium oxysporum IFO 5942,
Fusarium semitectum IFO 30200,
Gibberella fujikuroi IFO 6349,
Gliocladium cantenulatum IFO 6121,
Myrothecium roridum IFO 9531,
Nectria elegans IFO 7187,
Neurospora crassa IFO 6067,
Penicillium chrysogenum IFO 4626,
Rhizopus oryzae IFO 4706,
Schizophyllum commune IFO 4928,
Sporothrix schenckii IFO 5983,
Tuberculina persicinia IFO 6464,
Verticillium malthousei IFO 6624, and
Volutella buxi IFO 6003 to produce D-pantoic acid, and then separating said D-pantoic acid from the reaction medium, converting it into D-pantolactone, and recovering said D-pantolactone.

17. A process for preparing D-pantolactone, comprising subjecting D,L-pantolactone to selective asymmetric hydrolysis by contacting said D,L-pantolactone with a microorganism possessing the ability to effect selective asymmetric hydrolysis of only D-pantolactone in said D,L-pantolactone selected from the group consisting of the genera Fusarium, Cylindrocarpon, Gibberella, Aspergillus, Volutella, and Gliocladium to produce D-pantoic acid, and then separating said D-pantoic acid from the reaction medium, converting said D-pantoic acid into D-pantolactone, and recovering said D-pantolactone, wherein said microorganism is grown aerobically in a medium for a period of 1 to 7 days, at a pH of 3 to 9, at a temperature of 10° to 50° C.

* * * * *